United States Patent
Awad et al.

(10) Patent No.: US 9,850,133 B2
(45) Date of Patent: Dec. 26, 2017

(54) **GREEN SYNTHESIS OF REDUCED GRAPHENE OXIDE USING *NIGELLA SATIVA* SEED EXTRACT**

(71) Applicant: KING SAUD UNIVERSITY, Riyadh (SA)

(72) Inventors: Manal Ahmed Gasmelseed Awad, Riyadh (SA); Awatif Ahmed Hendi, Riyadh (SA); Khalid Mustafa Osman Ortashi, Riyadh (SA); Amel Laref, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/597,261

(22) Filed: May 17, 2017

(65) Prior Publication Data

US 2017/0327381 A1 Nov. 16, 2017

Related U.S. Application Data

(62) Division of application No. 15/151,466, filed on May 10, 2016, now Pat. No. 9,688,539.

(51) Int. Cl.
*C01B 31/04* (2006.01)
*A61K 31/336* (2006.01)
*A01N 43/20* (2006.01)
*C12P 17/02* (2006.01)

(52) U.S. Cl.
CPC ............ *C01B 31/043* (2013.01); *A01N 43/20* (2013.01); *A61K 31/336* (2013.01); *C12P 17/02* (2013.01)

(58) Field of Classification Search
CPC ... C01B 31/043; C01B 31/04; C01B 31/0407; C01B 31/0415; C01B 2204/00; C01B 2204/02; C01B 2204/04; C01B 2204/06; C01B 2204/065; C01B 2204/20; C01B 2204/22; C01B 2204/24; C01B 2204/28; C01B 2204/30; C01B 2204/32; A01N 43/20; A61K 31/336; C12P 17/02
USPC ........................................................ 423/448
See application file for complete search history.

(56) References Cited

U.S. PATENT DOCUMENTS 9,023,308 B2    5/2015   Shankman

FOREIGN PATENT DOCUMENTS

CN           104591173         5/2015

*Primary Examiner* — Daniel C McCracken
(74) *Attorney, Agent, or Firm* — Richard C. Litman

(57) ABSTRACT

The green synthesis of reduced graphene oxide nanoparticles using *Nigella sativa* seed extract comprises the steps of mixing a quantity of soot or other carbon source in an acid solution while stirring to obtain a solution; adding a first oxidant gradually into the solution to oxidize the soot and obtain a suspension; stirring the suspension while maintaining the temperature of the suspension at about 35° C.; adding *Nigella sativa* seed extract to the suspension while raising the temperature of the suspension to about 60° C.; adding hydrogen peroxide to the suspension; and isolating the reduced graphene oxide nanoparticles by centrifugation.

2 Claims, 9 Drawing Sheets

GREEN SYNTHESIS OF REDUCED GRAPHENE OXIDE USING NIGELLA SATIVA SEED EXTRACT

CROSS-REFERENCE TO RELATED APPLICATIONS

This application is a division of Ser. No. 15/151,466, filed May 10, 2016, now pending.

BACKGROUND OF THE INVENTION

1. Field of the Invention

The present invention relates to graphene oxide, and particularly to the green synthesis of reduced graphene oxide (rGO) using *Nigella sativa* seed extract and its applications.

2. Description of the Related Art

One of the recent advances in pharmacological research has been the use of novel drug delivery systems, and also the increasing application of monoclonal antibodies and oligonucleotides for therapeutic purpose. Functionalized nano-sized graphene has been used as a drug carrier for in vitro intracellular delivery of anticancer chemotherapy drugs. It has been found that nano-graphene with a biocompatible polyethylene glycol (PEG) coating displays high passive in vivo tumor uptake and could be used for effective photothermal ablation of tumors in a mouse model. On the other hand, many groups have developed graphene-based biosensors to detect various biomolecules via different mechanisms. Graphene-based nanomedicine, although still in its infancy, appears to be encouraging and may bring novel opportunities for future disease diagnosis and treatment.

Graphene is an atom-thick monolayer of carbon atoms arranged in a two dimensional honeycomb structure, and it is a basic building block for other graphitic materials, such as graphite and carbon nanotubes. Because of their unique and desirable electrical, optical, mechanical and chemical characteristics, graphene, graphene oxide (GO), and reduced graphene oxide (rGO) have been extensively studied for a variety of applications, such as nanoelectronics, sensors, energy storage, nanocomposites, etc., including biomedicine. The potential of graphene as a nanocarrier for drug delivery, gene delivery and nanomedicine has been demonstrated for possible cancer therapies. In addition, the improved synthesis and versatile surface modification of graphene has opened up new avenues for research on the nanoscale. In this regard, using "green" methods in the synthesis of nanoparticles has received attention, as conventional chemical methods are expensive and require the use of hazardous chemical and organic solvents.

Thus, the green synthesis of reduced graphene oxide (rGO) nanoparticles using *Nigella sativa* seed extract solving the aforementioned problems is desired.

SUMMARY OF THE INVENTION

The green synthesis of reduced graphene oxide nanoparticles using *Nigella sativa* seed extract comprises the steps of mixing a quantity of soot or other carbon source in an acid solution while stirring to obtain a solution; adding a first oxidant gradually into the solution to oxidize the soot and obtain a suspension; stirring the suspension while maintaining the temperature of the suspension at about 35° C.; adding *Nigella sativa* seed extract to the suspension while raising the temperature of the suspension to about 60° C.; adding hydrogen peroxide to the suspension; and isolating the reduced graphene oxide nanoparticles by centrifugation. The method of synthesizing reduced graphene oxide nanoparticles can further comprise washing the reduced graphene oxide nanoparticles with deionized water and 5% HCl solution and drying the product at about 100° C. in an oven.

The reduced graphene oxide nanoparticles can be used in inhibiting cancer cell proliferation. For example, the method of inhibiting the growth or proliferation of a cancer cell may comprise the step of contacting the cancer cell with an effective amount of the reduced graphene oxide nanoparticles. The cancer cell can include a breast carcinoma cell or a colon carcinoma cell.

The reduced graphene oxide nanoparticles can be used in inhibiting microbial activity. For example, a method for inhibiting microbial activity caused by a microorganism comprises the step of administering an effective amount of the graphene oxide nanoparticles to a site of microbial activity. The microorganisms can be selected from the group consisting of yeast, gram positive and gram negative bacteria.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
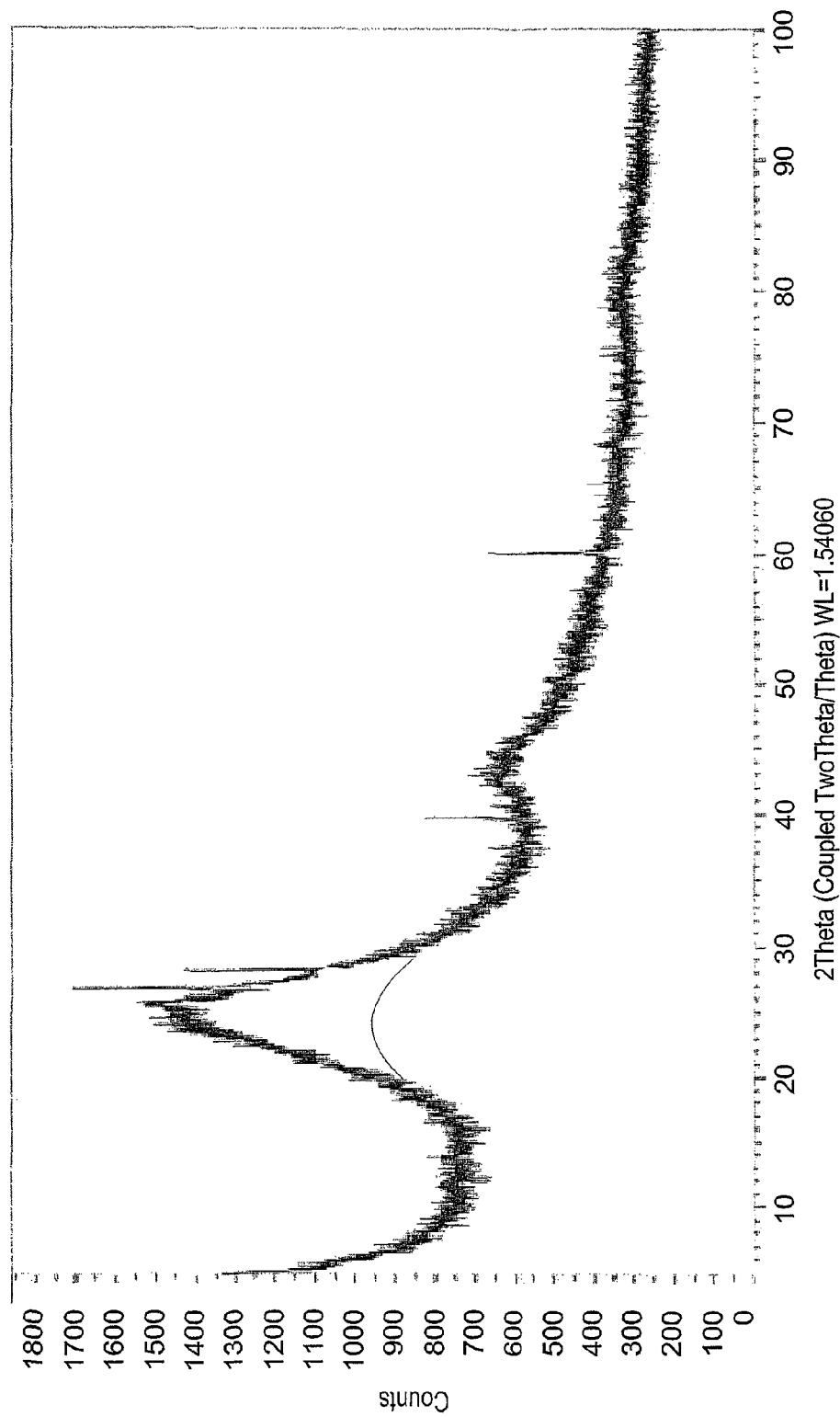
FIG. 1 is the X-ray diffraction pattern of reduced graphene oxide produced by green synthesis using *Nigella sativa* seed extract according to the present invention.

The green synthesis of reduced graphene oxide nanoparticles using *Nigella sativa* seed extract comprises the steps of mixing a quantity of soot or other carbon source in an acid solution while stirring to obtain a solution; adding a first oxidant gradually into the solution to oxidize the soot and obtain a suspension; stirring the suspension while maintaining the temperature of the suspension at about 35° C.; adding *Nigella sativa* seed extract to the suspension while raising the temperature of the suspension to about 60° C.; adding hydrogen peroxide to the suspension; and isolating the reduced graphene oxide nanoparticles by centrifugation.

The method of synthesizing reduced graphene oxide nanoparticles can further comprise washing the reduced graphene oxide nanoparticles with deionized water and 5% HCl solution and drying the product at about 100° C. in an oven. The carbon source for producing the reduced graphene oxide can be soot collected from girdle, which is formed during bakery. The acid can be sulfuric acid. The plant seeds extract used in the synthesis of reduced graphene oxide nanoparticles are obtained from the plant Nigella sativa. Generally, adding the Nigella sativa seed extract can be performed at a temperature of the suspension of about 60° C. for about 15 minutes. Typically, the first oxidant is potassium permanganate.

The reduced graphene oxide, which is produced from the synthesis method, are nanoparticles having a mean diameter in the range of from about 5 nm to about 100 nm across the largest dimension. Typically, the graphene oxide nanoparticles can have one or more shapes selected from the group consisting of spherical-shaped, spheroidal-shaped, elongated/spherical shaped, rod-shaped and faceted shaped.

The reduced graphene oxide nanoparticles can be used in inhibiting cancer cell proliferation. For example, a method of inhibiting the growth or proliferation of a cancer cell can comprise the step of contacting the cancer cell with an effective amount of the reduced graphene oxide nanoparticles. The cancer cell can include a breast carcinoma cell or a colon carcinoma cell.

The reduced graphene oxide nanoparticles can also be used in inhibiting microbial activity. For example, a method for inhibiting microbial activity caused by microorganisms comprises the step of administering an effective amount of the graphene oxide nanoparticles to a site of microbial activity. The microorganisms can be selected from the group consisting of yeast, gram positive and gram negative bacteria.

As used herein the tell "nanoparticle" refers to a particle having at least one dimension sized between 1 and 100 nanometers. By the term "effective amount", it is understood that, with respect to, for example, pharmaceuticals, a pharmaceutically effective amount is contemplated. A pharmaceutically effective amount is the amount or quantity of active ingredient that is enough for the required or desired therapeutic response, or in other words, the amount that is sufficient to elicit an appreciable biological response when administered to a patient.

As used herein, the term "seed extract" encompasses, for example, any chemical or combination of chemicals found in the seeds of the plant, including the derivatives of the compounds found in the seeds via chemical reaction. The "seed extract" can be obtained from the plant by any process, for example, cold water extraction, hot water extraction, extraction with an organic solvent, and/or extraction with a supercritical solvent. The preferred method of extraction of Nigella sativa seed extract is using boiling water as described below.

Nigella sativa, often called black cumin, is an annual flowering plant in the family Ranunculaceae, native to south and southwest Asia. Nigella sativa grows to 20-30 cm tall, with finely divided, linear leaves.

The present teachings will be understood more readily by reference to the following examples, which are provided by way of illustration.

Example 1

Preparation of Extract from Nigella Sativa Seeds

Nigella sativa seeds were washed several times with distilled water. Then, about 30 grams of coarsely ground Nigella sativa seeds were taken and boiled in 150 mL of double distilled water for about 5 min. The extract was centrifuged and then filtered. The filtrate was collected and stored at 4° C. until further use.

Example 2

Green Synthesis of Reduced Graphene Oxide (rGO) Nanoparticles

Soot was collected from girdle which formed during bakery of Abray, a local and traditional paste used as drinker in Ramadan month in Sudan. Graphene oxide (GO) was prepared according to the modified Hummer method. In detail, 1 g of soot was mixed with 50 mL $H_2SO_4$ and stirred for 5 min. Next, 5 g of potassium permanganate, $KMnO_4$, was very slowly added in an ice bath. The suspension was again stirred at 35° C. for 10 min. The temperature of the mixture was adjusted to a constant 60° C. for 15 min while the Nigella sativa seeds extract was added continuously so that the volume of the suspension was 150 mL, and 5 mL of $H_2O_2$ was added after 5 min. The reaction product was centrifuged and washed with deionized water and 5% HCl solution repeatedly. Finally, the product was dried at 100° C.

Figure 2:
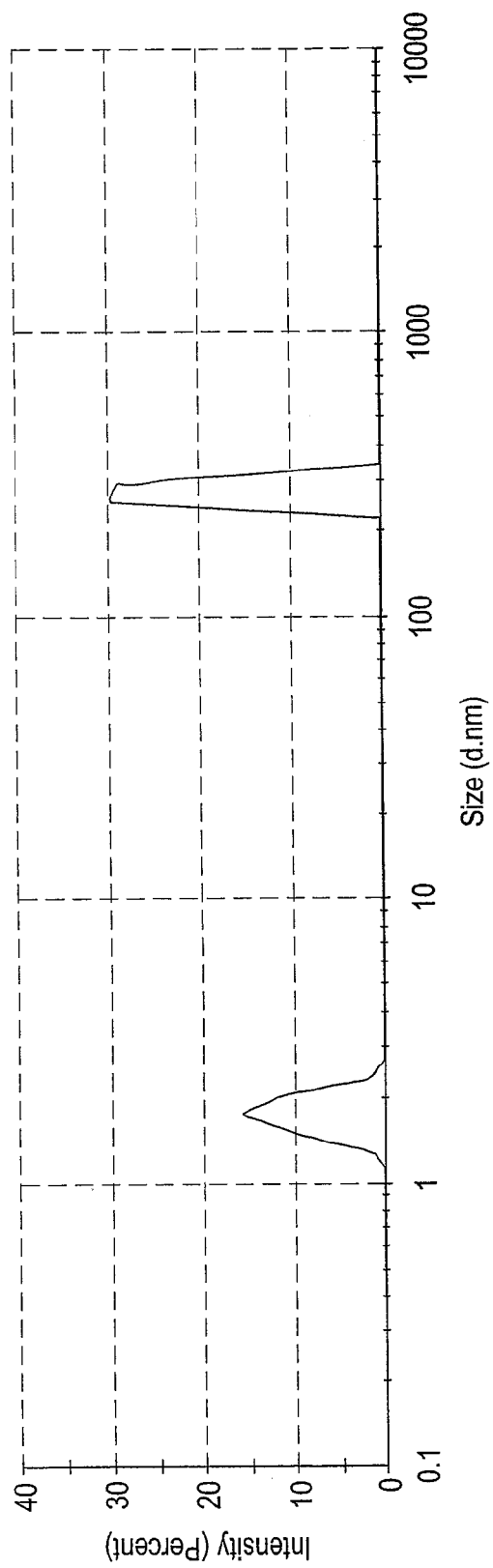
FIG. 2 is a Zetasizer plot showing particle size distribution of green synthesized reduced graphene oxide using *Nigella sativa* seed extract according to the present invention.
Figure 3A:
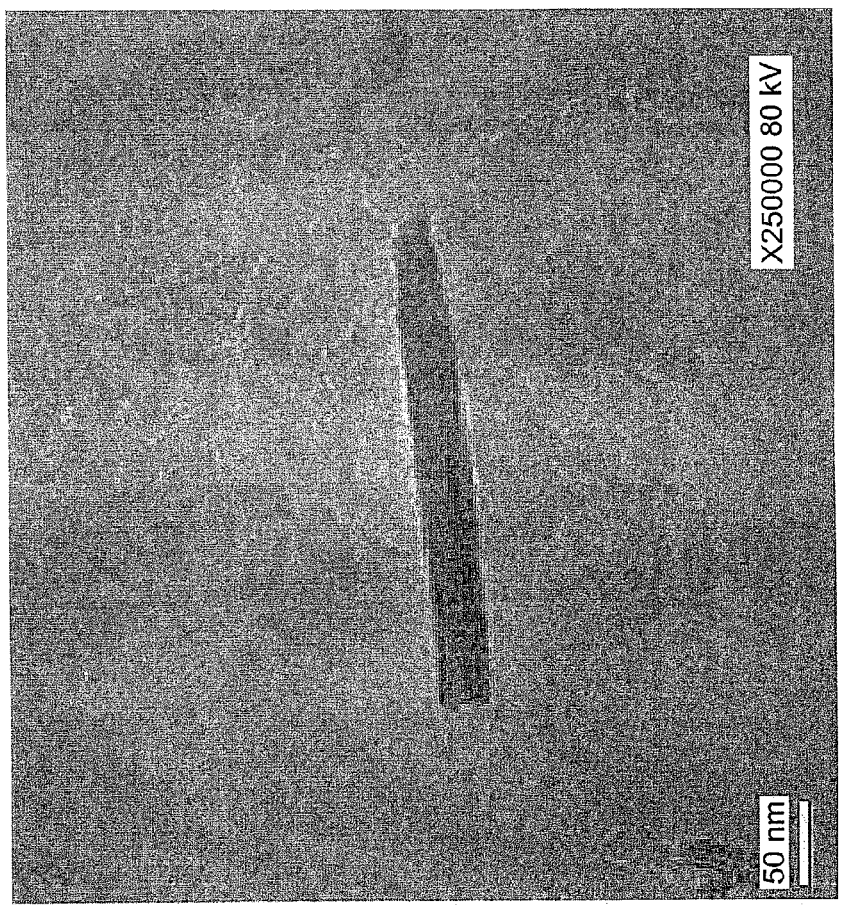
FIGS. 3A, 3B, and 3C are transmission electron micrographs (TEM) of green synthesized reduced graphene oxide using *Nigella sativa* seeds extract according to the present invention.
Figure 3B:
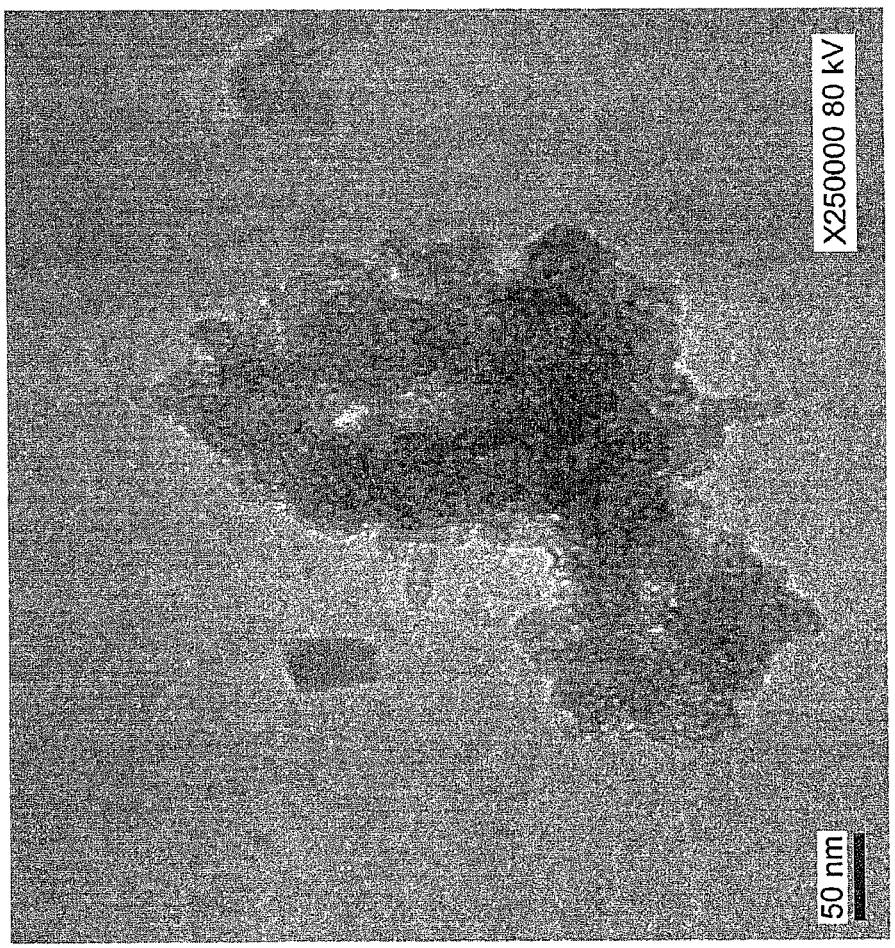
Figure 3C:
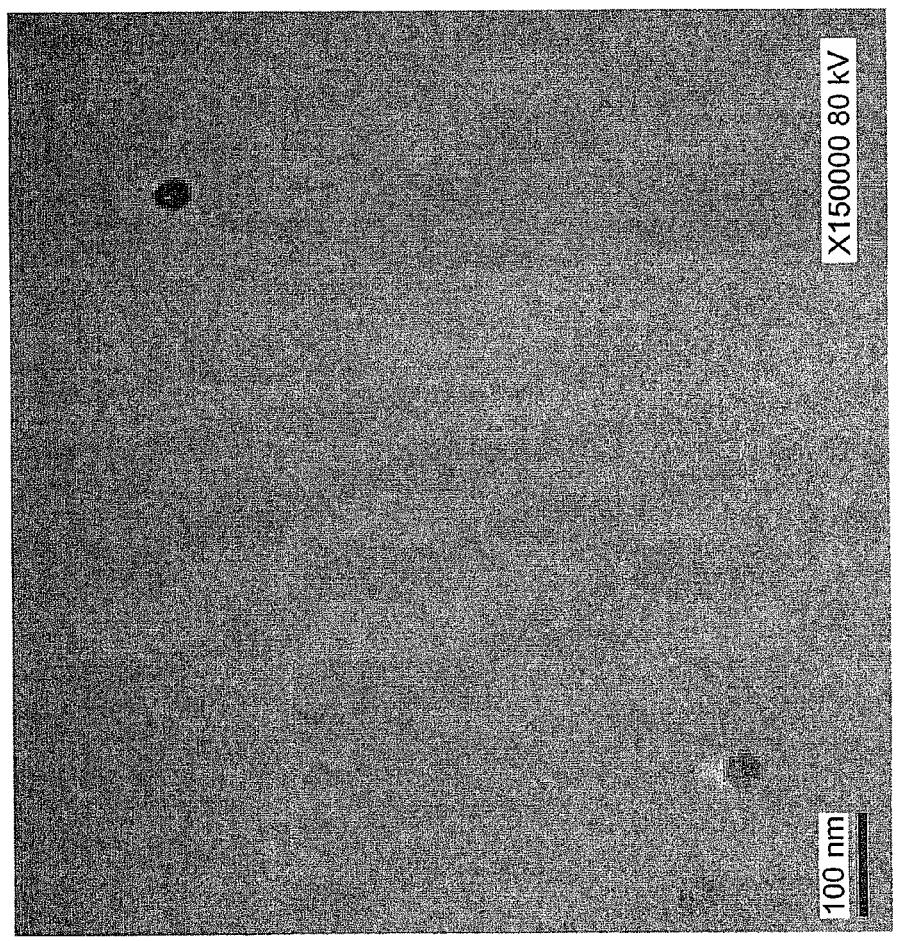
Figure 4A:
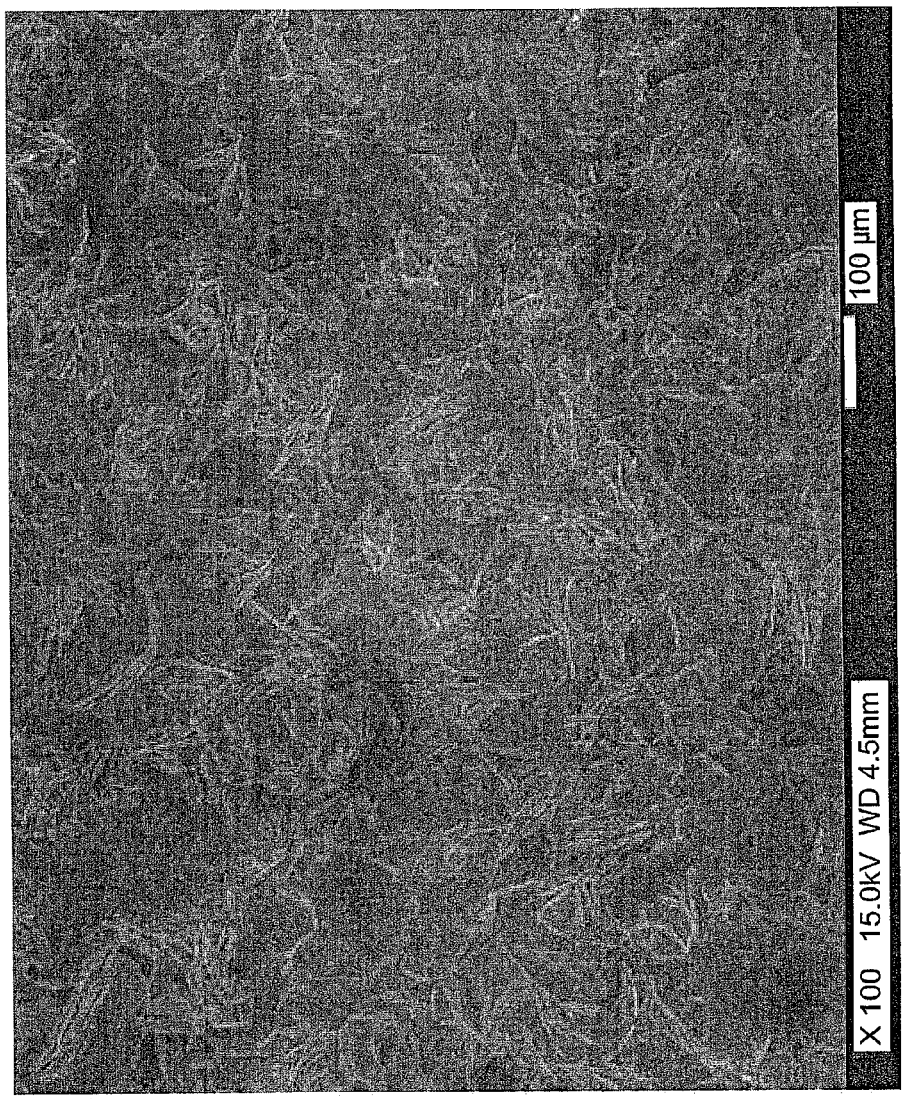
FIGS. 4A and 4B are scanning electron micrographs (SEM) of green synthesized reduced graphene oxide using *Nigella sativa* seeds extract according to the present invention at different levels of magnification.
Figure 4B:
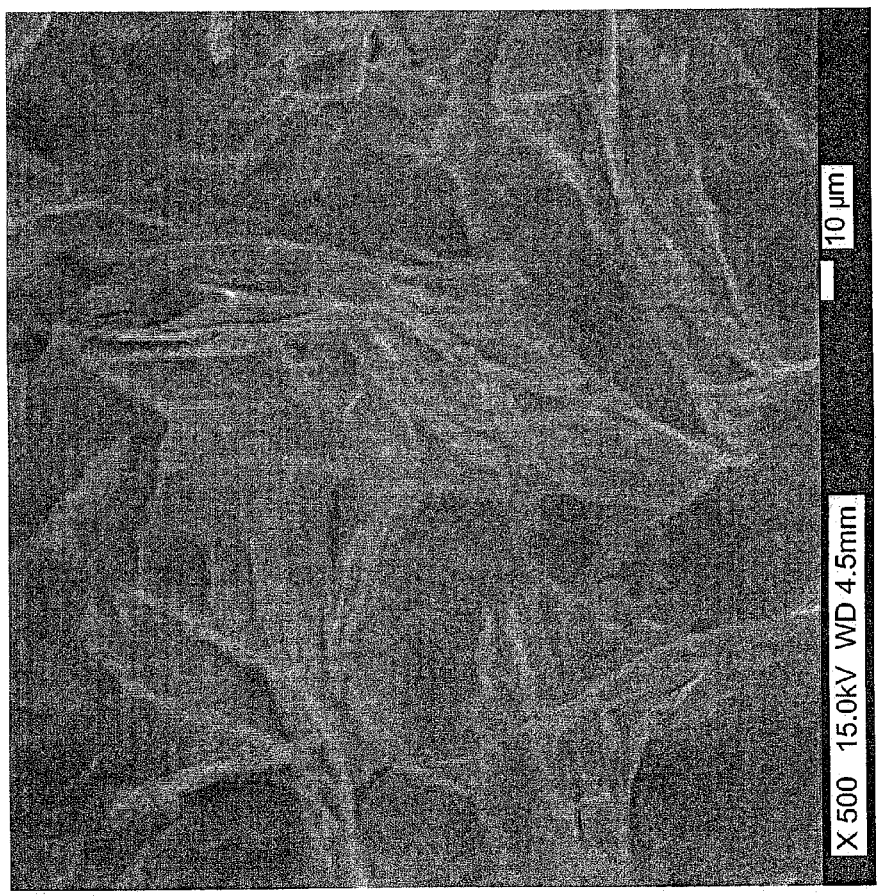
Figure 5:
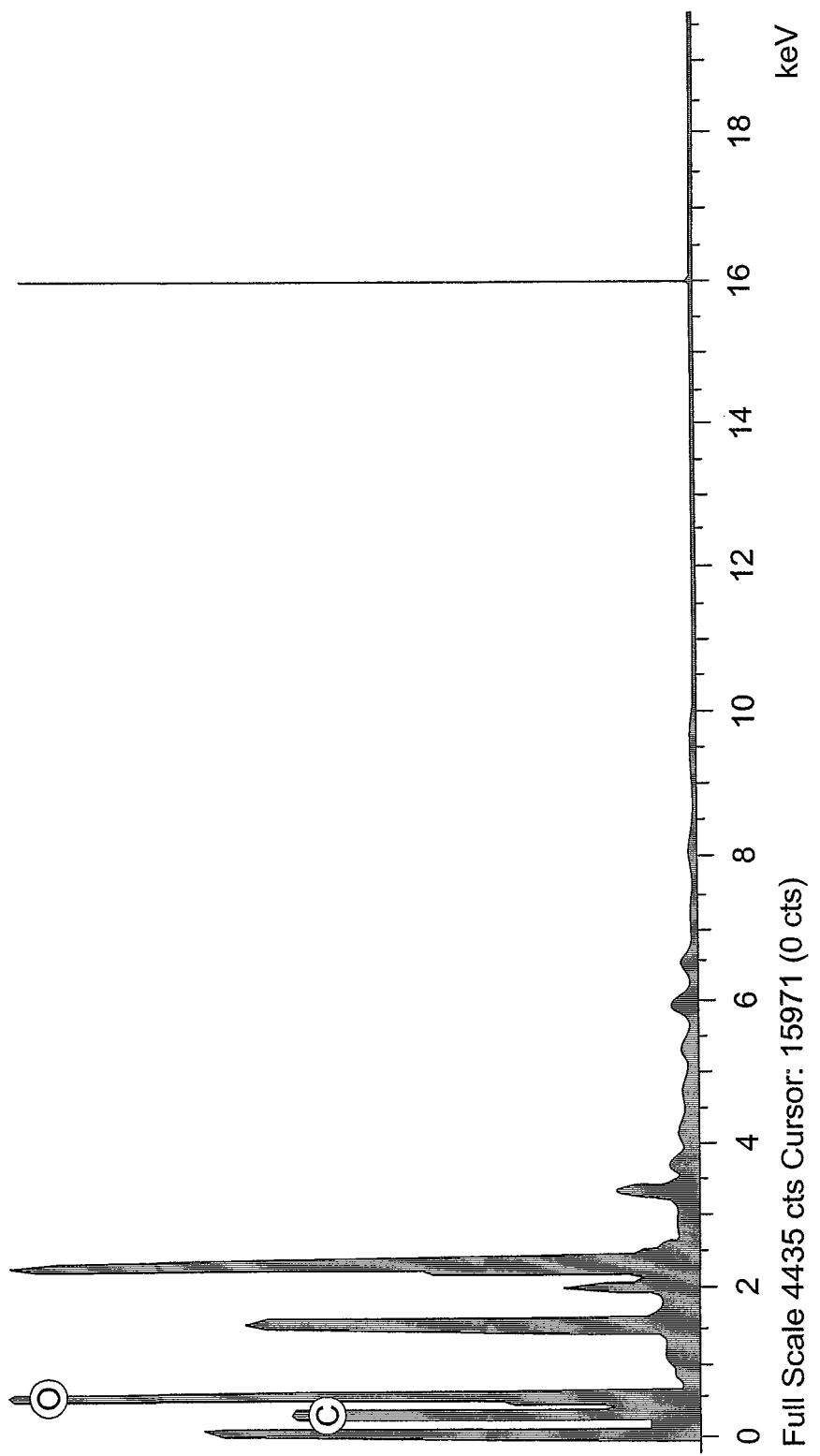
FIG. 5 is the Energy Dispersive Spectroscopy spectrum of green synthesized reduced graphene oxide using *Nigella sativa* seed extract according to the present invention with two dominant peaks for carbon and oxygen atoms, respectively.

The product was characterized by transmission electron microscopy (JEM-1011, JEOL, Japan). Also, scanning electron microscopy (SEM) was employed to characterize the shape and morphologies of font led nanoparticles using JEOL-FE SEM and X-ray diffractometer (XRD), Bruker D8 ADVANCE. The size of the synthesized nanoparticles was analyzed through Zetasizer, Nano series, HT Laser, ZEN3600 (Molvern Instrument, UK). JEOL-FE SEM; and Energy Dispersive Spectrometer (EDS) analysis was performed for the confirmation of elemental oxygen and carbon. FIG. 1 shows the XRD pattern of green synthesized reduced graphene oxide using Nigella sativa seed extract. FIG. 2 shows the particle size distribution of green synthesized reduced graphene oxide using Nigella sativa seed extract. Two peaks having Z-average sizes of about 1.8 nm (peak 1) and 300 nm (peak 2) having intensities of about 15% and 30% respectively were found. FIGS. 3A-C show the transmission electron microscopy (TEM) images of green synthesized reduced graphene oxide using Nigella sativa seed extract. The particles can be spherical or elongated or rod-like, with a dimension of about 5 nm to 200 nm. FIG. 4 shows the scanning electron microscopy (SEM) images of green synthesized reduced graphene oxide using Nigella sativa seed extract. Energy Dispersive Spectrometer (EDS) analysis was performed for the confirmation of elemental oxygen and carbon, as shown in FIG. 5. Table 1 shows the EDS results showing percentage of elements present in reduced graphene oxide nanoparticles suspension.

TABLE 1

Elemental analysis of reduced graphene oxide

| Element | Weight % | Atomic % |
|---|---|---|
| C | 8.45 | 10.77 |
| O | 87.42 | 83.66 |
| TOTALS | 100.00 | |

Example 3

Antimicrobial Screening

Antimicrobial activity of the reduced graphene oxide (rGO) nanoparticles was determined using the agar well diffusion assay method as described by Holder and Boyce, 1994. Three bacterial strains (two gram positive and one gram negative) and one yeast strain, namely, *Bacillis subtilis* (RCMB 010067), *Staphylococcus pneumoniae* (RCMB 010011), *Escherichia coli* (RCMB 010052), and *Aspergillus fumigatus* (RCMB 02568) were used for the antimicrobial assay.

The tested organisms were sub-cultured on nutrient agar medium (Oxoid laboratories, UK) for bacteria and Sabouraud dextrose agar (Oxoid laboratories, UK) for fungi. Ampicillin and Gentamicin were used as positive control for gram positive and gram negative bacteria, respectively, while Amphotericin B was used for fungi. The plates were done in triplicates. Bacterial cultures were incubated at 37° C. for 24 h, while the fungal cultures were incubated at 25-30° C. for 3-7 days. Antimicrobial activity was determined by measuring the zone of inhibition [A. Agwa, (2000)]. Samples were tested at a concentration of 100 µl; Data are expressed in the form of (M±S.D.): mean±standard deviation; Diameter of the inhibition zone (mm) beyond the well diameter of 6 mm; NT: not tested; NA: no activity. Table 2 shows the antimicrobial activity of green synthesized reduced graphene oxide nanoparticles suspension using diffusion agar well diffusion assay method.

TABLE 2

| | Nigella sativa reduced graphene oxide | Antibiotic |
|---|---|---|
| FUNGI | | Amphotericin B |
| *Aspergillus fumigatus* (RCMB 02567) | 33.3 ± 1.5 | 21.7 ± 1.5 |
| *Candida albicans* (RCMB 05038) | 19.3 ± 1.5 | 22.7 ± 1.5 |
| Gram Positive Bacteria: | | Ampicillin |
| *Streptococcus pneumoniae* (RCMB 010011) | 32.7 ± 2.1 | 21.0 ± 1.0 |
| *Bacillis subtilis* (RCMB 010068) | 34.0 ± 2.0 | 31.3 ± 1.5 |
| Gram negativeBacteria: | | Gentamicin |
| *Pseudomonas aeruginosa* (RCMB 010045) | 16.3 ± 2.1 | 16.0 ± 1.0 |
| *Escherichia coli* (RCMB 010054) | 26.3 ± 2.1 | 20.3 ± 0.58 |

Example 4

Antitumor Activity Assay

The tested human carcinoma cell lines were obtained from the American Type Culture Collection (ATCC, Rockville, Md.). The cells were grown on RPMI-1640 medium supplemented with 10% inactivated fetal calf serum and 50 µg/ml gentamycin. The cells were maintained at 37° C. in a humidified atmosphere with 5% $CO_2$ and were subcultured two to three times a week.

For antitumor assays, the tumor cell lines were suspended in medium at concentration $5 \times 10^4$ cell/well in Corning® 96-well tissue culture plates then incubated for 24 h. The tested compounds were then added into 96-well plates (six replicates) to achieve eight concentrations for each compound. Six vehicle controls with media or 0.5% DMSO were run for each 96 well plate as a control. After incubating for 24 h, the numbers of viable cells were determined by the MTT test. Briefly, the media was removed from the 96 well plates and replaced with 100 µl of fresh culture RPMI 1640 medium without phenol red then 10 µl of the 12 mM MTT stock solution (5 mg of MTT in 1 mL of PBS) to each well including the untreated controls. The 96 well plates were then incubated at 37° C. and 5% $CO_2$ for 4 hours. An 85 µl aliquot of the media was removed from the wells, and 50 µl of DMSO was added to each well and mixed thoroughly with the pipette and incubated at 37° C. for 10 min. Then, the optical density was measured at 590 nm with the microplate reader (SunRise, TECAN, Inc., USA) to determine the number of viable cells and the percentage of viability was calculated using the following equation (1):

$$\text{Percentage of Viability} = \left[1 - \frac{ODt}{ODc}\right] \times 100 \qquad (1)$$

Figure 6:
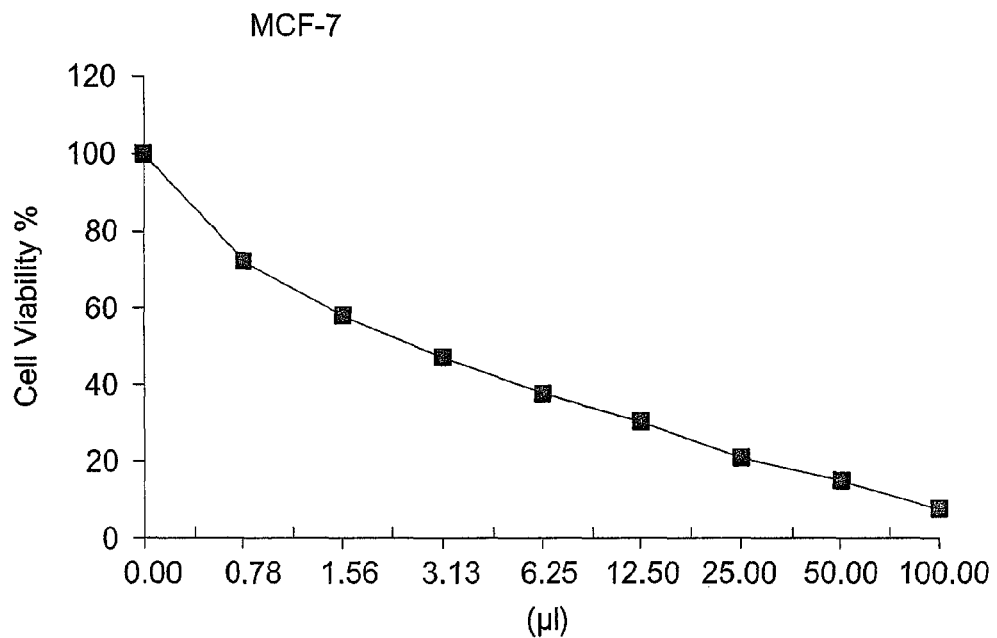
FIG. 6 is a plot of cell viability as a function of the concentration of reduced graphene oxide synthesized from *Nigella sativa* seeds extract according to the present invention for breast carcinoma cells (MCF-7 cell line).

In Equation 1, ODt is the mean optical density of wells treated with the tested sample and ODc is the mean optical density of untreated cells. The relation between surviving cells and drug concentration is plotted to get the survival curve of each tumor cell line after treatment with the specified compound. The 50% inhibitory concentration ($IC_{50}$), the concentration required to cause toxic effects in 50% of intact cells, was estimated from graphic plots of the dose response curve for each conc. using Graphpad Prism software (San Diego, Calif. USA) (Mosmann, 1983; Elaasser et al., 2011). FIG. 6 shows the cytotoxic activity of reduced graphene Oxide synthesized from *Nigella sativa* seeds extract suspension against Breast carcinoma cells (MCF-7 cell line). Table 3 shows the inhibitory activity of reduced graphene Oxide synthesized from *Nigella sativa* extract against breast carcinoma cells was detected under these experimental conditions with $IC_{50}$=2.67 µl.

TABLE 3

| Sample | Viability % (3 Replicates) | | | | Inhibition | Standard Deviation |
|---|---|---|---|---|---|---|
| Conc. (µl) | 1st | 2nd | rd | Mean | % | (±) |
| 100 | 7.92 | 6.84 | 7.13 | 7.30 | 92.70 | 0.56 |
| 50 | 13.85 | 14.87 | 15.41 | 14.71 | 85.29 | 0.79 |
| 25 | 20.42 | 18.56 | 22.98 | 20.65 | 79.35 | 2.22 |
| 12.5 | 28.93 | 29.71 | 31.86 | 30.17 | 69.83 | 1.52 |
| 6.25 | 34.82 | 37.15 | 40.72 | 37.56 | 62.44 | 2.97 |
| 3.125 | 45.49 | 46.73 | 48.24 | 46.82 | 53.18 | 1.38 |
| 1.56 | 57.13 | 54.89 | 61.82 | 57.95 | 42.05 | 3.54 |
| 0.78 | 74.59 | 69.27 | 72.16 | 72.01 | 27.99 | 2.66 |
| 0 | 100 | 100 | 100 | 100 | 0.00 | |

Figure 7:
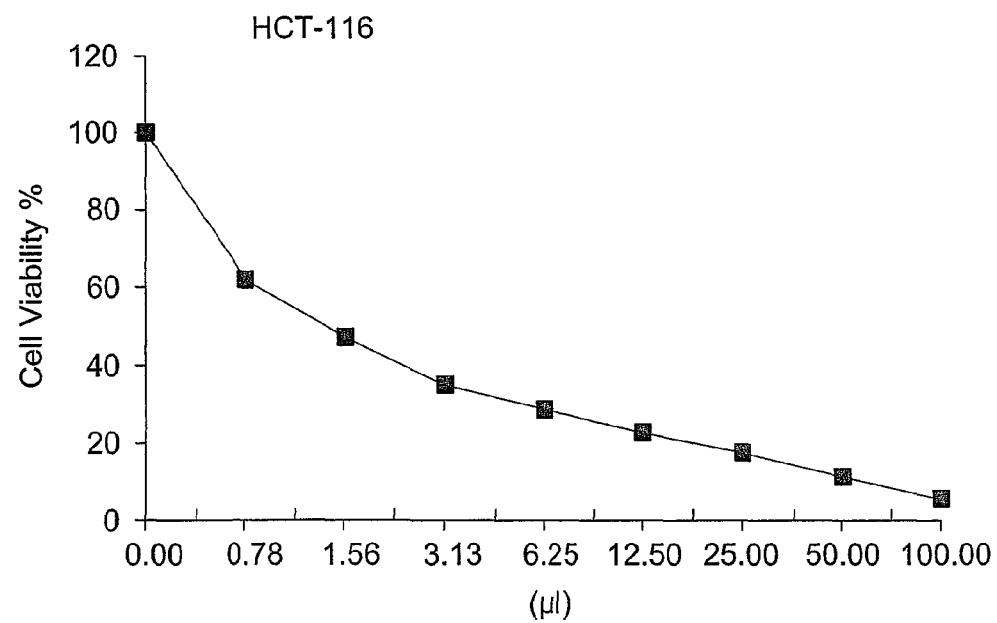
FIG. 7 is a plot of cell viability as a function of the concentration of reduced graphene oxide synthesized from *Nigella sativa* seeds extract according to the present invention for colon carcinoma cells (HCT-116 cell line).

FIG. 7 shows the cytotoxic activity of reduced graphene oxide synthesized from *Nigella sativa* seeds extract suspension against colon carcinoma cells (HCT-116 cell line).

Table 4 shows the inhibitory activity of reduced graphene Oxide synthesized from *Nigella sativa* extract against colon carcinoma cells was detected under these experimental conditions with $IC_{50}=1.41$ μl.

TABLE 4

| Sample conc. (μl) | Viability % (3 Replicates) | | | | Inhibition % | Standard Deviation (±) |
|---|---|---|---|---|---|---|
| | 1st | 2nd | 3rd | Mean | | |
| 100 | 5.92 | 6.49 | 5.38 | 5.93 | 94.07 | 0.56 |
| 50 | 12.88 | 11.36 | 10.74 | 11.66 | 88.34 | 1.10 |
| 25 | 17.75 | 16.45 | 18.52 | 17.57 | 82.43 | 1.05 |
| 12.5 | 22.91 | 23.67 | 21.74 | 22.77 | 77.23 | 0.97 |
| 6.25 | 26.74 | 30.68 | 28.91 | 28.78 | 71.22 | 1.97 |
| 3.125 | 32.65 | 37.94 | 35.13 | 35.24 | 64.76 | 2.65 |
| 1.56 | 39.87 | 48.96 | 53.12 | 47.32 | 52.68 | 6.78 |
| 0.78 | 58.72 | 63.21 | 60.84 | 60.92 | 39.08 | 2.25 |
| 0 | 100 | 100 | 100 | 100 | 0.00 | |

Thus, the above examples illustrate a simple, non-toxic, cost-effective, quick, and environmentally friendly synthesis approach for the reduced graphene oxide nanoparticles using *Nigella sativa* seeds extract. The potential of graphene as nanocarriers for drug delivery, gene delivery and nanomedicine exists for possible cancer therapies. The green method of synthesizing the reduced graphene oxide nanoparticles can have potential applications as antibacterial and anticancer agents.

It is to be understood that the present invention is not limited to the embodiments described above, but encompasses any and all embodiments within the scope of the following claims.

We claim:
1. Reduced graphene oxide nanoparticles produced according to a method for green synthesis of reduced graphene oxide, the method comprising the steps of: a) mixing a quantity of carbon source in an acid while stirring to obtain a solution, b) adding a first oxidant gradually into the solution to oxidize the carbon source and obtain a suspension, c) stirring the suspension while maintaining a temperature of the suspension at about 35° C., d) adding *Nigella sativa* seed extract to the suspension while raising the temperature of the suspension to about 60° C., and e) adding hydrogen peroxide to the suspension; and isolating resulting reduced graphene oxide nanoparticles by centrifugation, wherein the graphene oxide nanoparticles have a mean diameter between 5 nm and 200 nm across the largest dimension and consist essentially of the *Nigella sativa* seed extract.

2. The reduced graphene oxide nanoparticles according to claim 1, wherein said graphene oxide nanoparticles have a shape selected from the group consisting of spherical-shaped, spheroidal-shaped, elongated/spherical shaped, rod-shaped and faceted shaped.

* * * * *